United States Patent
Ohri et al.

(10) Patent No.: US 9,445,795 B2
(45) Date of Patent: Sep. 20, 2016

(54) PREVENTION OF PREMATURE GELLING OF DELIVERY DEVICES FOR PH DEPENDENT FORMING MATERIALS

(75) Inventors: Rachit Ohri, Framingham, MA (US); Phillip Blaskovich, Salem, MA (US)

(73) Assignee: Confluent Surgical, Inc., Waltham, MA (US)

( * ) Notice: Subject to any disclaimer, the term of this patent is extended or adjusted under 35 U.S.C. 154(b) by 1288 days.

(21) Appl. No.: 12/724,448

(22) Filed: Mar. 16, 2010

(65) Prior Publication Data

US 2011/0092899 A1     Apr. 21, 2011

Related U.S. Application Data

(60) Provisional application No. 61/252,268, filed on Oct. 16, 2009.

(51) Int. Cl.
*A61M 25/14* (2006.01)
*A61M 25/00* (2006.01)
*A61B 17/00* (2006.01)

(52) U.S. Cl.
CPC ............ *A61B 17/00491* (2013.01); *A61B 2017/00495* (2013.01); *A61B 2017/00522* (2013.01)

(58) Field of Classification Search
CPC ............ A61B 17/00491; A61B 2017/00495; A61B 2017/00522
USPC ............ 604/82, 89, 191, 225, 272, 284; 424/422
See application file for complete search history.

(56) References Cited

U.S. PATENT DOCUMENTS

| | | | |
|---|---|---|---|
| 4,359,049 A | | 11/1982 | Redl et al. |
| 4,359,079 A | * | 11/1982 | Bledsoe .............. E06B 9/40 160/121.1 |
| 4,631,055 A | * | 12/1986 | Redl .............. A61B 17/00491 222/135 |
| 4,735,616 A | * | 4/1988 | Eibl .............. A61B 17/00491 604/191 |
| 4,874,368 A | * | 10/1989 | Miller .............. A61B 17/00491 222/137 |
| 4,902,281 A | | 2/1990 | Avoy |
| 4,932,942 A | * | 6/1990 | Maslanka .............. A61B 1/12 604/164.09 |
| 4,978,336 A | * | 12/1990 | Capozzi et al. .............. 604/82 |
| 5,116,315 A | * | 5/1992 | Capozzi .............. A61B 17/00491 222/137 |

(Continued)

FOREIGN PATENT DOCUMENTS

| | | |
|---|---|---|
| EP | 1 795 215 A2 | 6/2007 |
| EP | 2 143 737 A1 | 1/2010 |

(Continued)

OTHER PUBLICATIONS

European Search Report for EP 10251803.3-2310 date of completion is Jan. 25, 2011 (3 pages).

(Continued)

*Primary Examiner* — Quynh-Nhu H Vu
(74) *Attorney, Agent, or Firm* — Carter Deluca Farrell and Schmidt, LLP (57) ABSTRACT

The present disclosure provides treatment of an apparatus, in embodiments a delivery device, which prevents premature gelling of any materials or precursor(s) of a pH dependent forming material, in embodiments a hydrogel, dispensed by the delivery device. The pH microenvironment near the surface of a lumen of the device, in embodiments the tip of a spray applicator through which the material to be dispensed is expelled from the device, may be controlled to prevent premature gelling.

22 Claims, 8 Drawing Sheets

(56) References Cited

U.S. PATENT DOCUMENTS

| | | | |
|---|---|---|---|
| 5,162,430 A | | 11/1992 | Rhee et al. |
| 5,290,228 A | * | 3/1994 | Uemura .................. A61M 5/19 604/220 |
| 5,324,775 A | | 6/1994 | Rhee et al. |
| 5,410,016 A | | 4/1995 | Hubbell et al. |
| 5,514,379 A | | 5/1996 | Weissleder et al. |
| 5,543,441 A | | 8/1996 | Rhee et al. |
| 5,550,187 A | | 8/1996 | Rhee et al. |
| 5,605,255 A | * | 2/1997 | Reidel ............. A61B 17/00491 222/137 |
| 5,752,974 A | | 5/1998 | Rhee et al. |
| 5,874,500 A | | 2/1999 | Rhee et al. |
| 6,123,685 A | * | 9/2000 | Reynolds ........................ 604/90 |
| 6,143,352 A | | 11/2000 | Clark et al. |
| 6,152,943 A | * | 11/2000 | Sawhney ......... A61B 17/12022 604/284 |
| 6,165,201 A | | 12/2000 | Sawhney et al. |
| 6,179,862 B1 | | 1/2001 | Sawhney |
| 6,514,534 B1 | | 2/2003 | Sawhney |
| 6,566,406 B1 | | 5/2003 | Pathak et al. |
| 6,605,294 B2 | | 8/2003 | Sawhney |
| 6,656,200 B2 | | 12/2003 | Li et al. |
| 6,673,093 B1 | * | 1/2004 | Sawhney ......... A61B 17/00491 604/240 |
| 6,703,047 B2 | | 3/2004 | Sawhney et al. |
| 6,802,822 B1 | * | 10/2004 | Dodge ............. A61B 17/00491 604/82 |
| 6,818,018 B1 | | 11/2004 | Sawhney |
| 7,009,034 B2 | | 3/2006 | Pathak et al. |
| 7,332,566 B2 | | 2/2008 | Pathak et al. |
| 7,347,850 B2 | | 3/2008 | Sawhney |
| 7,901,395 B2 | * | 3/2011 | Borden ............. A61M 25/0009 604/284 |
| 7,914,484 B2 | * | 3/2011 | Yokoyama ...................... 604/83 |
| 2004/0106896 A1 | * | 6/2004 | Lee ...................... A61K 38/363 604/82 |
| 2005/0096588 A1 | * | 5/2005 | Hagmann ........ A61B 17/00491 604/82 |
| 2006/0099256 A1 | | 5/2006 | Price et al. |
| 2006/0105012 A1 | * | 5/2006 | Chinn et al. .................. 424/422 |
| 2006/0229571 A1 | * | 10/2006 | Peppel .................. A61M 39/26 604/256 |
| 2006/0253082 A1 | * | 11/2006 | McIntosh ......... A61B 17/00491 604/191 |
| 2007/0160504 A1 | * | 7/2007 | Parthasarathy et al. ...... 422/102 |
| 2008/0108824 A1 | | 5/2008 | Isch et al. |
| 2008/0114092 A1 | | 5/2008 | Sawhney |
| 2008/0124400 A1 | | 5/2008 | Liggins et al. |
| 2008/0195040 A1 | | 8/2008 | Clark et al. |
| 2008/0214695 A1 | | 9/2008 | Pathak et al. |
| 2008/0247987 A1 | | 10/2008 | Liggins et al. |
| 2008/0260802 A1 | | 10/2008 | Sawhney et al. |
| 2009/0012465 A1 | * | 1/2009 | Latini ............................. 604/82 |
| 2009/0076459 A1 | * | 3/2009 | Goldberg ......... A61B 17/00491 604/191 |
| 2009/0268546 A1 | | 10/2009 | Reinprecht |

FOREIGN PATENT DOCUMENTS

| | | |
|---|---|---|
| EP | 2 196 193 A1 | 6/2010 |
| EP | 2 233 160 A2 | 9/2010 |
| EP | 2 233 161 A2 | 9/2010 |
| WO | WO 00/59516 A1 | 10/2000 |
| WO | WO 03/090683 A2 | 11/2003 |
| WO | WO 2008/033964 A2 | 3/2008 |

OTHER PUBLICATIONS

Agi, et al, "Fluorescence Monitoring of the Microenvironmental pH of Highly Charged Polymers," Journal of Polymer Science, Part A, Polymer Chemistry, pp. 2105-2110 (1997).

Tatavarti, et al., "Microenvironmental pH Modulation Based Release Enhancement of a Weakly Basic Drug from Hydrophilic Matrices," Journal of Pharmaceutical Sciences, vol. 95, No. 7, pp. 1459-1468 (2006).

Liermann, et al. "Microenvironments of pH in Biofilms Grown on Dissolving Silicate Surfaces," Chemical Geology 171, pp. 1-16 (2000).

Korostynska et al. "Review Paper: Materials and Techniques for In Vivo pH Monitoring," IEEE Sensors Journal, vol. 8, No. 1, pp. 20-28 (2008).

Ruiz-Ederra, et al., "In Situ Fluorescence Measurement of Tear Film $[Na^+]$, $[K^+]$, $[Cl^-]$, and pH in Mice Shows Marked Hypertonicity in Aquaporin-5 Deficiency," Investigative Ophthalmology & Visual Science, vol. 50, No. 5, pp. 2132-2138 (2009).

Grant, et al., "A Sol-gel Based Fiber Optic Sensor for Local Blood pH Measurements," Sensors and Actuators, B 45, pp. 35-42 (1997).

Korostynska et al. "Review on State-of-the-art in Polymer Based pH Sensors," Sensors, vol. 7, pp. 3027-3042 (2007).

Bladbjerg et al., "Activity of Recombinant Factor VIIa under Different Conditions In Vitro: Effect of Temperature, pH, and Haemodilution," Blood Coagulation and Fibrinolysis, vol. 19, No. 5, pp. 369-374 (2008).

Norris et al., "Blood Coagulation," Best Pract Res Clin Obstet Gynaecol., vol. 17, No. 3, pp. 369-383 (2003).

Wiernicki et al., "Elastin Degradation within the Abdominal Aortic Aneurysm Wall—Relationship Between Intramural pH and Adjacent Thrombus Formation," European Journal of Clinical Investigation, vol. 38, No. 12, pp. 883-887 (2008).

Thomas et al., "High Molecular Weight Kininogen Adsorption on Hemodialysis Membranes: Influence of pH and Relationship with Contact Phase Activation of Blood Plasma. Influence of Pretreatment with poly(ethyleneimine)," International Journal of Artificial Organs, vol. 23, No. 1, pp. 20-26 (2000).

Tatavarti et al., "Influence of Methacrylic and Acrylic Acid Polymers on the Release Performance of Weakly Basic Drugs from Sustained Release Hydrophilic Matrices," Journal of Pharmaceutical Sciences, vol. 93, No. 9, pp. 2319-2331 (2004).

Tran et al. "Modulation of Microenvironmental pH and Crystallinity of Ionizable Telmisartan Using Alkalizers in Solid Dispersions for Controlled Release," Journal of Controlled Release, vol. 129, pp. 59-65 (2008).

European Search Report for EP 11250308.1-1219 date of completion is Nov. 21, 2011 (3 pages).

Y. Takemoto et al.: "Human Placental Ectonucleoside Triphosphate Diphosphohydrolase Gene Transfer via Gelatin-Coated Stents Prevents In-Stent Thrombosis" Arteriosclerosis, Thrombosis, and Vascular Biology, vol. 29, No. 6, Mar. 26, 2009, pp. 857-862.

International Search Report issued in Application EP 11250562.3 mailed Dec. 8, 2011.

International Search Report issued in Application EP 11250564.9 mailed Dec. 8, 2011.

International Search Report issued in Application EP 11250563.1 mailed Dec. 27, 2011.

International Search Report issued in Application EP 11250566.4 mailed Dec. 22, 2011.

International Search Report issued in Application EP 11250565.6 mailed Dec. 23, 2011.

* cited by examiner

PREVENTION OF PREMATURE GELLING OF DELIVERY DEVICES FOR PH DEPENDENT FORMING MATERIALS

CROSS-REFERENCE TO RELATED APPLICATIONS

This application claims priority to U.S. Provisional Patent Application Ser. No. 61/252,268 filed on Oct. 16, 2009, the disclosure of which is hereby incorporated by reference in its entirety.

TECHNICAL FIELD

The present disclosure relates to apparatus for applying hydrogels within the body. More particularly, the present disclosure relates to apparatus and methods for delivering two or more liquid precursors to form a hydrogel implant in situ, with treatments to the delivery device and/or precursors being delivered to minimize premature gelling and/or clogging of the delivery device.

BACKGROUND OF RELATED ART

Various compositions are utilized in situ to seal defects and/or leaks, as well as adsorb body fluids, including blood. For example, materials utilized in situ include hemostats, adhesives, sealants, hydrogels, combinations thereof, and the like.

Hydrogels are materials that absorb solvents (such as water), undergo rapid swelling without discernible dissolution, and maintain three-dimensional networks capable of reversible deformation.

One issue that may arise with the delivery of materials capable of forming adhesives, sealants, hemostats, hydrogels, and the like, in situ, is that the precursors utilized to form the material may begin to gel during dispensing from any delivery device, which may clog the dispensing apparatus utilized to deliver the hydrogel. For example, some adhesives, hydrogels, and sealants that are produced upon the admixture of more than one precursor may, depending upon the pH of the local environment, gel within about 3.5 seconds after the precursors have contacted each other. Changes in the pH of the local environment may alter the reaction kinetics of such adhesives, hydrogels and sealants to speed up or slow down gelling of the precursors.

Thus, conventional devices utilized to deliver such materials often come with multiple tips, which may have to be changed during a surgical procedure, due to premature gelling and clogging. Similarly, for devices which dispense such materials without the use of a tip, premature gelling and clogging may result in the failure of the applicator system or suboptimal performance during a surgical procedure.

It would be desirable to provide methods and apparatus for introducing materials capable of forming in situ that avoid premature gelling and/or clogging of the dispensing or delivery device.

SUMMARY OF THE DISCLOSURE

The present disclosure provides treatment of an apparatus, in embodiments a delivery device, which prevents premature gelling of any materials or precursor(s) of a pH dependent forming material, in embodiments a hydrogel. In embodiments, a delivery device of the present disclosure may include at least one lumen, a means for aiding in expelling materials from the lumen, and an opening through which the materials may be expelled from the delivery device in vivo, wherein at least a portion of a surface of the delivery device has a surface functionality capable of modulating the pH of the microenvironment near the surface.

In other embodiments, a delivery device of the present disclosure may also include a manifold configured for operable engagement with at least a first and a second source of precursor of the material, the manifold including at least a first and second precursor channel therethrough, and a tip assembly, wherein the tip assembly is configured to receive a mixture comprising the at least first and second precursors prior to the mixture being expelled from the opening defined in a distal end of the tip assembly.

In yet other embodiments, a delivery device of the present disclosure may also include an elongated shaft extending distally from the manifold, the elongated shaft including at least a first and a second precursor lumen extending the length thereof, the at least first and second precursor lumens in fluid communication with the at least first and second precursor channels.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

In accordance with the present disclosure, delivery systems for depositing pH dependent forming materials are provided, which may be treated to prevent premature gelling of the precursor(s) utilized to form such materials. Examples of such materials, referred to, in embodiments, as "pH dependent forming materials", include, but are not limited to, hemostats, adhesives, sealants, hydrogels, combinations thereof, and the like. The pH dependent forming materials may be formed from a single precursor, or multiple precursors.

In accordance with the present disclosure, the pH of a surface of a delivery device utilized to dispense the pH dependent forming material, as well as the pH of the microenvironment near the surface of the device, may be adjusted so that the precursor(s) of the pH dependent forming material do not prematurely gel. As used herein, "microenvironment" includes the area near the surface of a device which may exhibit a pH that is close to, but different than, the bulk pH of the environment in which the device is placed. In embodiments, the surface of a delivery device may possess a functionality capable of modulating the pH of the materials near the surface, as well as the pH of the microenvironment near the surface of the device. Thus, if the precursor(s) of the pH dependent forming material gel at an acidic pH, the surface of the delivery device, as well as the pH of the microenvironment near the surface of the device, may possess a slightly more basic pH to avoid premature gelling. Alternatively, if the precursor(s) of the pH dependent forming material gel at a more basic pH, the surface of the delivery device, as well as the pH of the microenvironment near the surface of the device, may possess a slightly more acidic pH to avoid premature gelling.

In some embodiments, the pH of the surface of the delivery device and the microenvironment near the surface may be adjusted by imparting a charge thereto. A charge may be imparted to the surface of a delivery device by admixing a material capable of imparting a charge to the material utilized to form the delivery device, in embodiments a polymer, or by applying a coating including a material capable of imparting a charge to a surface of the delivery device. In other embodiments, the delivery device may have surface functional groups capable of modulating the pH of the materials at or near the surface of the device. The ability to modulate local pH and/or to have pH buffering capacity in the microenvironment near the surface will allow retardation of the rate of in situ formation, and therefore avoid clogging.

For example, the local pH microenvironment of a surface of a delivery device, as well as the pH of the microenvironment near the surface of the device, due to the presence of the charged polymer and/or functional group, may be from about 3 to about 11, in embodiments from about 5 to about 9.

Any surface of a delivery device that may come into contact with a precursor of a pH dependent forming material may be treated in accordance with the present disclosure.

pH Dependent Forming Materials

The methods and delivery devices of the present disclosure may be utilized for the dispensing of any pH dependent forming material. The pH dependent forming material may include a single precursor or multiple precursors that form "in situ", meaning formation occurs at a tissue in a living animal or human body, or the pH dependent forming materials may form ex vivo, and then be implanted into a living animal or human body. In general, this may be accomplished by having a precursor that can be activated at the time of application to form a pH dependent forming material, in embodiments a hydrogel.

In embodiments, the methods and devices of the present disclosure may be especially beneficial for treating delivery devices used to deliver pH dependent forming materials that may undergo premature gelling and clogging. Such devices may include applicators that come with multiple tips, which may have to be changed during a surgical procedure, due to premature gelling and clogging when the precursors mix in the tip. Similarly, for devices which dispense such materials without the use of a tip, premature gelling and clogging may be avoided. In either case, the potential failure of the applicator system or suboptimal performance during a surgical procedure of such a system may be avoided, as the need to start/stop delivery of the precursor(s), which may lead to the formation of two or more layers, gels with reduced strength or performance, uneven coatings, combinations thereof, and the like, does not occur as the device does not clog. Moreover, the time for application of the pH dependent forming material may be reduced.

pH dependent forming materials may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including temperature, pH, ionic strength, combinations thereof, and the like. Chemical (covalent) crosslinking may be accomplished by any of a number of mechanisms, including free radical polymerization, condensation polymerization, anionic or cationic polymerization, step growth polymerization, electrophile-nucleophile reactions, combinations thereof, and the like.

In some embodiments; pH dependent forming material systems may include those biocompatible multi-precursor systems that spontaneously crosslink when the precursors are mixed, but wherein the two or more precursors are individually stable for the duration of the deposition process. Such systems include, for example for a hydrogel, a first precursor including macromers that are di or multifunctional amines and a second precursor including di or multifunctional oxirane containing moieties.

Some embodiments of forming a pH dependent forming material involve mixing precursors that crosslink quickly after application to a surface, e.g., on a tissue of a patient, to form a pH dependent forming material.

The crosslinking reaction leading to gelation can occur, in some embodiments within a time from about 1 second to about 5 minutes, in embodiments from about 3 seconds to about 1 minute; persons of ordinary skill in these arts will immediately appreciate that all ranges and values within these explicitly stated ranges are contemplated. In some cases gelation may occur in less than about 3.5 seconds.

The precursors may be placed into solution prior to use, with the solution being delivered to the patient. Solutions suitable for use in accordance with the principles of the present disclosure include those that may be used to form implants in lumens or voids. Where two solutions are employed, each solution may contain one precursor of a pH dependent forming material which forms upon on contact. The solutions may be separately stored and mixed when delivered into a tissue lumen.

Additionally, any solutions utilized as part of the pH dependent forming material system should not contain harmful or toxic solvents. In embodiments, the precursor(s) may be substantially soluble in a solvent such as water to allow application in a physiologically-compatible solution, such as buffered isotonic saline. Water-soluble coatings may form thin films, but in embodiments may also form three-dimensional gels of controlled thickness. The gel may also be biodegradable, so that it does not have to be retrieved from the body. Biodegradability, as used herein, refers to the predictable disintegration of the coating into molecules small enough to be metabolized or excreted under normal physiological conditions.

Properties of the pH dependent forming material system may be selected according to the intended application. For example, if the pH dependent forming material is to be used to temporarily occlude a reproductive organ, such as a fallopian tube, it may be desirable that the pH dependent forming material system undergo significant swelling and be biodegradable. Alternatively, the pH dependent forming material may have thrombotic properties, or its precursors may react with blood or other body fluids to form a coagulum.

Other applications may require different characteristics of the pH dependent forming material system. Generally, the materials should be selected on the basis of exhibited biocompatibility and lack of toxicity.

Certain properties of the pH dependent forming material can be useful, including adhesion to a variety of tissues, desirable setting times to enable a surgeon to accurately and conveniently place the pH dependent forming materials, high water content for biocompatibility, which may be relevant for hydrogels, mechanical strength for use in sealants, and/or toughness to resist destruction after placement. Synthetic materials that are readily sterilized and avoid the dangers of disease transmission involved in the use of natural materials may thus be used. Indeed, certain in situ polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, pH dependent forming materials may be made from one or more precursors. The precursor may be, e.g., a monomer or a macromer. One type of precursor may have a functional group that is ethylenically unsaturated. An ethylenically unsaturated functional group may be polymerized using an initiator to start the reaction. Precursors with at least two ethylenically unsaturated functional groups may form crosslinked polymers. Some compositions have certain precursors with only one such functional group and additional crosslinker precursors with a plurality of functional groups for crosslinking the precursors. Ethylenically unsaturated functional groups may be polymerized by various techniques, e.g., free radical, condensation, or addition polymerization.

pH dependent forming materials may thus be formed from one precursor (as by free radical polymerization), two precursors, or made with three or more precursors, with one or more of the precursors participating in crosslinking to form the pH dependent forming material.

Another type of precursor has a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits reaction (e.g., as relating to pH or solvent), the functional groups react with each other to form covalent bonds. The precursors become crosslinked when at least some of the precursors can react with more than one other precursor. For instance, a precursor with two functional groups of a first type may be reacted with a crosslinking precursor that has at least three functional groups of a second type capable of reacting with the first type of functional groups.

In embodiments, a pH dependent forming material may be a hydrogel. As mentioned above, in embodiments the hydrogel may be formed from single precursors or multiple precursors. For example, where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors may have biologically inert and water soluble cores. When the core is a polymeric region that is water soluble, preferred polymers that may be used include: polyethers, for example, polyalkylene oxides such as polyethylene glycol ("PEG"), polyethylene oxide ("PEO"), polyethylene oxide-co-polypropylene oxide ("PPO"), and co-polyethylene oxide block or random copolymers; polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, and hydroxymethylcellulose; hyaluronic acid; and proteins such as albumin, collagen, casein, and gelatin. The polyethers, and more particularly, poly(oxyalkylenes) or poly(ethylene glycol) or polyethylene glycol, may be especially useful. When the core is small molecular in nature, any of a variety of hydrophilic functionalities can be used to make the first and second hydrogel precursors water soluble. For example, functional groups like hydroxyl, amine, sulfonate and carboxylate, which are water soluble, maybe used to make the precursor water soluble. In addition, N-hydroxysuccinimide ("NHS") ester of suberic acid is insoluble in water, but by adding a sulfonate group to the succinimide ring, the NHS ester of suberic acid may be made water soluble, without affecting its reactivity towards amine groups.

In embodiments, at least one of the first and second hydrogel precursors is a cross-linker. In embodiments, at least one of the first and second hydrogel precursors is a macromolecule, and is referred to as a "functional polymer".

In embodiments, the first precursor, the second precursor, or both, may be a polymer or non-polymer, and may be natural or synthetic. As used herein, "natural" or a "natural component" includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic recombinant materials, as well as methods capable of producing proteins with the same sequences as those found in nature and/or methods capable of producing materials with the same structure and components as natural materials, such as synthetic hyaluronic acid. For example, in embodiments, the natural component may be a small molecule, such as an amino acid or derivative thereof. Synthetic refers to a molecule not found in nature and does not include a derivatized version of a natural biomolecule, e.g., collagen with modified side groups. Polyamino acid polymers generated synthetically are normally considered to be synthetic if they are not found in nature and are engineered to not be identical to naturally occurring biomolecules. For instance, trilysine is synthetic since it is not found in nature (even though some bacteria might produce relatively larger polylysines). In some cases dilysines and/or tetralysines may also be utilized as one of the precursors.

Each of the first and second hydrogel precursors may be multifunctional, meaning that it may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

In embodiments, a multifunctional nucleophilic polymer such as trilysine may be used as a first hydrogel precursor and a multifunctional electrophilic polymer such as a multi-arm PEG functionalized with multiple NHS groups may be used as a second hydrogel precursor. The multi-arm PEG functionalized with multiple NHS groups can for example have four, six or eight arms and have a molecular weight from about 5,000 to about 25,000. Many other examples of suitable first and second hydrogel precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

In embodiments, one or more precursors having biodegradable linkages present in between functional groups may be included to make the hydrogel biodegradable or absorbable. In some embodiments, these linkages may be, for example, esters, which may be hydrolytically degraded in physiological solution. The use of such linkages is in contrast to protein linkages that may be degraded by proteolytic action. A biodegradable linkage optionally also may form a part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

In embodiments a pH dependent forming material may also include an initiator. An initiator may be any precursor or group capable of initiating a polymerization reaction for the formation of the pH dependent forming material.

Control of the pH

In embodiments, the delivery device, including any applicator tip, may be made of a polymeric material that is selected so that the pH of the surface of the delivery device, as well as the pH of the microenvironment near the surface of the delivery device, prevents premature gelling of the pH dependent material. In embodiments, the pH of the surface of the delivery device, as well as the pH of the microenvironment near the surface of the delivery device, may be influenced by a charge on the surface of the device. In other embodiments, functional groups may be present on a polymer utilized to form the delivery device or a coating thereon, thereby impacting the pH of the surface of the delivery device, as well as the pH of the microenvironment near the surface of the delivery device. These modifications may both affect the local pH, as well as the pH buffering capacity of the microenvironment near the surface of the device.

By forming the delivery device with materials capable of influencing pH, the pH of a surface of a delivery device utilized to dispense the pH dependent forming material, as well as the pH of the microenvironment near the surface of the delivery device, may be adjusted so that the precursor(s) of the pH dependent forming material do not prematurely gel. Thus, as noted above, if the precursor(s) of the pH dependent forming material gel at an acidic pH, the surface of the delivery device, as well as the pH of the microenvironment near the surface of the delivery device, may possess a slightly more basic pH to avoid premature gelling. Alternatively, if the precursor(s) of the pH dependent forming material gel at a more basic pH, the surface of the delivery device, as well as the pH of the microenvironment near the surface of the delivery device, may possess a slightly more acidic pH to avoid premature gelling.

In embodiments, it may be desirable to adjust the pH microenvironment of at least a tip of a delivery device utilized to dispense a pH dependent forming material.

In embodiments, the pH of the surface of a delivery device, as well as the pH of the microenvironment near the surface of the delivery device, may be altered utilizing a charged polymer to form the device, or by admixing a material capable of imparting a charge to the material utilized to form the delivery device, in embodiments a polymer. Methods for forming such polymers or combining materials with polymeric materials are within the purview of those skilled in the art and include blending, mixing, stirring, copolymerizing, combinations thereof, and the like.

In other embodiments, the pH of the surface of a delivery device, as well as the pH of the microenvironment near the surface of the delivery device, may be altered by applying a coating including a material capable of imparting a charge to a surface of the delivery device that may be in contact with precursors utilized to form a pH dependent forming material, including any lumen or any spray tip, to aid in controlling the local pH microenvironment. Such a coating would not affect the pH of the precursor(s) of the pH dependent forming material, or any solution containing such precursor(s), but would be applied to at least a portion of the surface of the delivery device in contact with the precursor(s) of the pH dependent forming material.

Methods for applying a coating are within the purview of those skilled in the art and include, but are not limited to, dipping, spraying, plasma deposition, combinations thereof, and the like.

Examples of charged polymers that may be utilized in forming a delivery device or a coating to be applied thereto include, but are not limited to, 2-hydroxyethyl methacrylate (HEMA), 2-acrylamido-2-methylpropane sulfonic acid (AAMPS), 3-methacryloylaminopropyl-trimethyl ammonium chloride (MAPTAC), N,N-diallyl-N,N-dimethyl ammonium chloride (DADMAC), combinations thereof, and the like.

Thus, for example, where the polymer is based upon MAPTAC, it will possess a positive charge due to the presence of a quaternary ammonium group, which remains cationic at all pH values. In embodiments, a copolymer of MAPTAC and HEMA may be utilized which attracts negatively charged low-molecular weight species such as hydroxyl ions and repels hydrogen ions. Such a copolymer may possess MAPTAC in an amount from about 0.1 percent by weight to about 10 percent by weight of the copolymer, and HEMA in an amount from about 90 percent by weight to about 99.9 percent by weight of the copolymer, with MAPTAC present in embodiments from about 0.2 percent by weight to about 5 percent by weight of the copolymer, with HEMA present from about 95 percent by weight to about 99.8 percent by weight of the copolymer.

Alternatively, where a charged polymer is based upon AAMPS, it will possess a negative charge due to the presence of its sulfonate group, which remains ionized even in highly acidic conditions. In embodiments, a copolymer of AAMPS in HEMA may be utilized which will thus attract hydrogen ions (or protons). Such a copolymer may possess AAMPS in an amount from about 0.1 percent by weight to about 10 percent by weight of the copolymer, with the HEMA present in an amount from about 90 percent by weight to about 99.9 percent by weight of the copolymer, in embodiments the AAMPS may be present in an amount from about 0.2 percent by weight to about 5 percent by weight of the copolymer, with the HEMA present in an amount from about 95 percent by weight to about 99.8 percent by weight of the copolymer.

In other embodiments, a charged polymer may be formed with hydroxypropyl methylcellulose, acrylic acid copolymers, maleic acid copolymers, methacrylic acid copolymers, and the like, including a copolymer of methacrylic acid with ethyl acrylate, combinations thereof, and the like. Copolymers of methacrylic acid with ethyl acrylate include those commercially available under the EUDRAGIT® name from Rohm Pharma Polymers (Piscataway, N.J.). In embodiments, these polymers may be charged by incorporation of an acid therein. Suitable acids which may be included in such copolymers may include, for example, citric acid, fumaric acid, succinic acid, malic acid, combinations thereof, and the like. Where an acid is added to a polymer to form a charged polymer, the acid may be added in an amount from about 0.1 percent by weight to about 10 percent by weight of the copolymer, in embodiments from about 0.5 percent by weight to about 5 percent by weight of the copolymer.

Other polymers may also be utilized. As noted above, in embodiments, a polymer may possess functional groups capable of altering the pH of a surface of a delivery device, as well as the pH of the microenvironment near the surface of the delivery device. For example, in embodiments, one could utilize the reaction of succinic anhydride with any hydroxyl or amine-functional polymer to generate a carboxylated polymer. Such polymers have an ability to affect the pH microenvironment when utilized to form a portion of a delivery device or a coating thereon, as they are capable of neutralizing bases through neutralization with the carboxylic acid group to form the carboxylic acid anion. A summary of this reaction is provided below:

-continued

In other embodiments, one could use glycidyl methacrylate (GMA) in copolymers to provide pendant epoxy functionality. The epoxy group has the ability to absorb acids (protons) and undergo a ring opening reaction, thus becoming protonated. Thus, such a copolymer also has the ability to affect the pH of an aqueous microenvironment. The relevant chemical structure is provided below for the GMA monomer, which is the precursor to the GMA polymer.

In yet other embodiments, acetoacetoxyethyl methacrylate (AAEM) copolymers may be utilized. AAEM copolymers can chelate a metal ion, in embodiments a divalent or multivalent ion, between its two carbonyl groups, which could then impart charge into the polymeric structure. Metal ions which could be chelated by such a copolymer include, but are not limited to, silver, cobalt, zinc, calcium, magnesium, platinum, tin, selenium, manganese, combinations thereof, and the like. In embodiments, an anionic (negative) charge may be created in a basic environment devoid of cations or metal ions. The relevant chemical structure is provided below for the AAEM monomer, which is the precursor to the AAEM polymer.

The formation of suitable copolymers is within the purview of those skilled in the art and may include the use of crosslinkers such as multi-functional acrylates or methacrylates, photoinitiators described above, in embodiments benzoin ethyl ethers, combinations thereof, and the like.

In accordance with the present disclosure, the local pH microenvironment of a surface of a delivery device, due to the presence of the surface functionality, may be from about 3 to about 11, in embodiments from about 5 to about 9. In some embodiments, the local pH microenvironment may be from about 6.0 to about 7.39 and in other embodiments from about 7.41 to about 8.5.

Methods for determining the pH microenvironment are within the purview of those skilled in the art and include, for example, amperometric and potentiometric microelectrodes, such as the ORION® microelectrodes by Thermo Fisher Scientific (Waltham, Mass.); optical and fluorescent pH sensors, including hollow fiber membranes micro probes; ion selective membranes; ion selective field effect transistors; two terminal micro sensors; metal oxide and conductometric pH-sensing devices; and confocal laser scanning microscopy (CLSM), a high resolution and non-invasive technique to monitor pH continuously and spatially resolved, as further disclosed by Agi, et al., "Fluorescence Monitoring of the Microenvironmental pH of Highly Charged Polymers," Journal of Polymer Science, Part A, Polymer Chemistry, pp. 2105-2110 (1997); Tatavarti, et al., "Microenvironmental pH Modulation Based Release Enhancement of a Weakly Basic Drug from Hydrophilic Matrices," Journal of Pharmaceutical Sciences, Vol. 95, No. 7, pp. 1459-1468 (2006); Liermann, et al. "Microenvironments of pH in Biofilms Grown on Dissolving Silicate Surfaces," Chemical Geology 171, pp. 1-16 (2000); Korostynska et al. "Review Paper: Materials and Techniques for In Vivo pH Monitoring," IEEE Sensors Journal, Vol. 8, No. 1, pp. 20-28 (2008); Ruiz-Ederra, et al., "In Situ Fluorescence Measurement of Tear Film [$Na^+$], [$K^+$], [$Cl^-$], and pH in Mice Shows Marked Hypertonicity in Aquaporin-5 Deficiency," Investigative Ophthalmology & Visual Science, Vol. 50, No. 5, pp. 2132-2138 (2009); Grant, et al., "A Sol-gel Based Fiber Optic Sensor for Local Blood pH Measurements," Sensors and Actuators, B 45, pp. 35-42 (1997); and Korostynska et al. "Review on State-of-the-art in Polymer Based pH Sensors," Sensors, Vol. 7, pp. 3027-3042 (2007), the entire disclosures of each of which are incorporated by reference herein.

Any device utilized to dispense pH dependent forming materials, including dual syringes suitable for applying precursor solutions, may benefit from the treatment of the present disclosure. By controlling the local pH microenvironment within the device and/or applicator, including at least a portion of any surface of any lumen within such delivery device that may be in contact with one or more precursors of a pH dependent forming material, in embodiments a spray tip, premature gelling of the precursors utilized to form the pH dependent forming material may be avoided. Thus, clogging of the delivery device, a common problem with applicators and delivery devices of pH dependent forming materials, may be avoided.

A delivery device may include, at a minimum, at least one lumen within which materials, in embodiments the precursor(s) utilized to form a pH dependent forming material, may be included, an opening through which the precursor(s) may be expelled from the lumen in vivo, and a means for aiding in the expulsion of the precursor(s), in embodiments the precursor(s) of the pH dependent forming material, from the lumen.

Utilizing the processes and concepts of the present disclosure, the pH microenvironment present within a delivery device, which can impact gel formation kinetics, may be altered such that gel formation is slowed down close to the surfaces of the device/applicator precursor(s), thus preventing clogging of the device.

Figure 1:
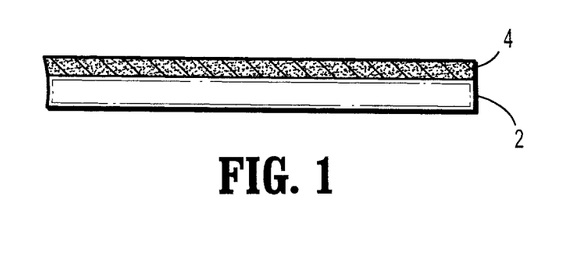
FIG. 1 is a side view of a surface of a delivery device of the present disclosure, depicting the microenvironment pH near the surface of the delivery device.

The effects obtained with the pH microenvironment according to the present disclosure may be localized and transient. As depicted in FIG. 1, surface 2 of a delivery device of the present disclosure may have a pH microenvironment 4 near the surface 2 of the delivery device. Thus, the effects obtained within the microenvironment 4 adjacent the surface 2 will not impact the bulk of the material (not shown in FIG. 1) flowing through the delivery device/applicator. Moreover, the pH microenvironment does not affect the reaction kinetics of the pH dependent forming material precursors outside the device/applicator or the physical properties of the gel.

Delivery Systems for Forming Hydrogel Implants In Situ

While the description below describes a spray tip assembly in detail, any device which may occlude, such as, for example stents, catheters, pacemaker leads, grafts, guidewires, or any other hollow devices which permit the flow of materials through the interior of the device, may benefit from the processes and treatments of the present disclosure.

In embodiments, one may use a dual syringe or similar device to apply the precursor solutions, such as those described in U.S. Pat. Nos. 4,874,368; 4,631,055; 4,735,616; 4,359,049; 4,978,336; 5,116,315; 4,902,281; 4,932,942; 6,179,862; 6,673,093; and 6,152,943. Further, such precursors may be used in combination with visualization agents such as a dye. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include FD&C Blue #1, FD&C Blue #2, FD&C Blue #3, D&C Green #6, methylene blue, combinations thereof, and the like.

Figure 2:
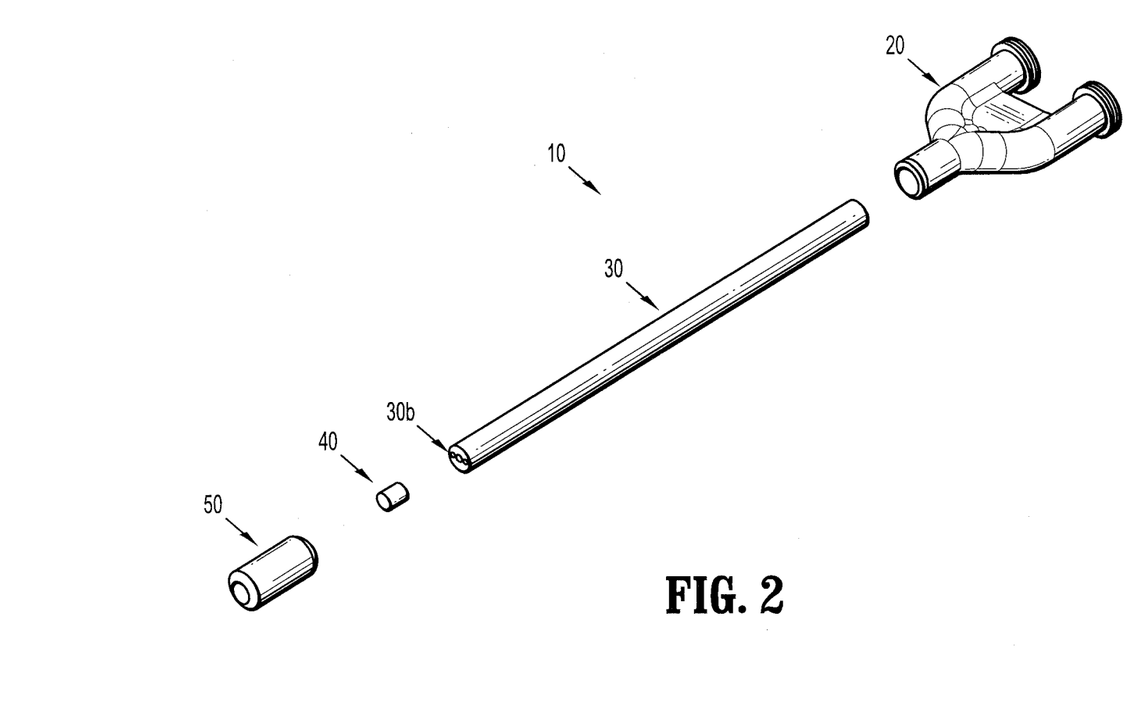
FIG. 2 is an exploded perspective view of an applicator assembly including a spray tip assembly according to an embodiment of the present disclosure.

In some embodiments, suitable delivery devices include those as depicted in the Figures. Referring initially to FIG. 2, an applicator assembly including a spray tip assembly according the present disclosure is shown generally as applicator assembly 10. Applicator assembly 10 includes a manifold or base 20, an elongated shaft 30 extending from manifold 20, and a spray tip assembly 50 positioned on a distal end 30b of elongated shaft 30. Applicator assembly 10 further includes an insert 40 configured to be received within spray tip assembly 50 and located distal of elongated shaft 30.

Figure 3:
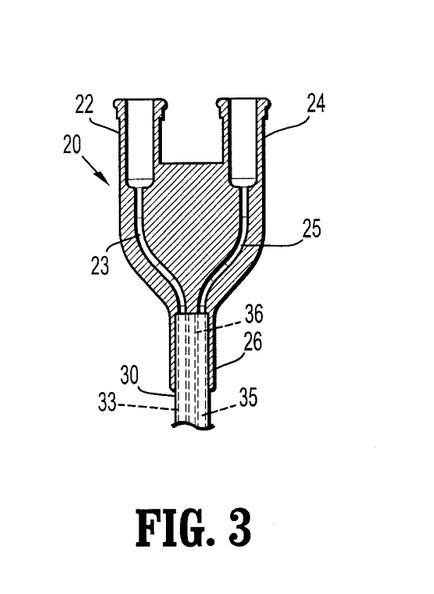
FIG. 3 is a cross-sectional side view of a manifold of the applicator assembly of FIG. 2.

With reference now to FIG. 3, manifold 20 includes a substantially Y-shaped member having a first and a second proximal extension 22, 24 and a distal extension 26. Proximal extensions 22, 24 are configured for operable engagement with a first and a second source of precursor (not show), e.g., a syringe. Distal extension 26 is configured for operable engagement with elongated shaft 30, as will be discussed in further detail below. Manifold 20 further includes first and second precursor channels 23, 25. First and second precursor channels 23, 25 fluidly communicate the first and second sources of precursors with a first and a second lumen 33, 35 formed in elongated shaft 30. While manifold 20, as shown, is configured to receive only two sources of precursor, it is envisioned that manifold 20 may be configured to receive more than two sources of precursor.

Referring back to FIG. 2, elongated shaft 30 may define a substantially solid body of silicone, plastic, polymer or other flexible material. As noted above, elongated shaft 30 includes first and second precursor lumens 33, 35 extending the length thereof. A wire 36 composed of a malleable material also extends the length of elongated shaft 30. Wire 36 is configured to maintain elongated shaft 30 in a bent or flexed configuration after elongated shaft 30 has been bent or flexed to accommodate a given procedure. Elongated shaft 30 is secured to distal extension 26 of manifold 20 such that first and second precursor lumens 33, 35 align with first and second precursor channels 23, 25, respectively. Alternatively, elongated shaft 30 may be integrally formed at a distal end of manifold 20. Elongated shaft 30 may further include grooves, detents, threads or otherwise be configured for secure engagement with spray tip assembly 50.

Figure 4:
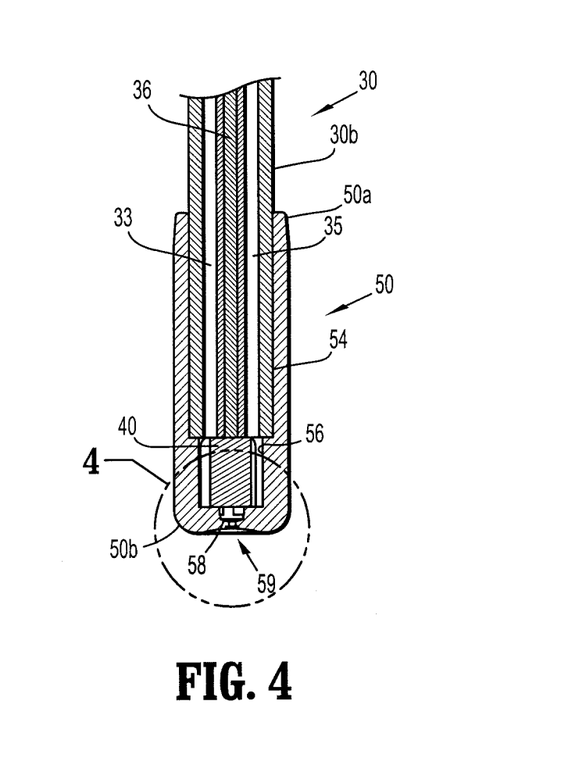
FIG. 4 is a cross-sectional side view of the spray tip assembly of the applicator assembly of FIG. 2.

With reference now to FIGS. 4-7, spray tip assembly 50 defines a substantially cylindrical body 52 having an open proximal end 52a and a substantially closed distal end 52b. Open proximal end 52a is configured to receive distal end 30b of elongated shaft 30 (FIG. 4). As will be discussed in further detail below, distal end 52b includes an outlet 59 configured to eject a thoroughly mixed solution. Spray tip assembly 50 may be composed of silicone or other suitable biocompatible material. Spray tip assembly 50 may be made from a polymer possessing a material capable of imparting a charge as described above, or may possess a coating with a material capable of imparting a charge as described above. The charge present on the surface of spray tip assembly 50 thus provides for control of the pH microenvironment of the delivery device, and prevent premature gelling of any pH dependent forming material dispensed from the device and/or clogging of the device.

Still referring to FIGS. 4-7, spray tip assembly 50 includes a first chamber 54, an intermediate chamber 56 and a final chamber 58. First chamber 54 defines a substantially cylindrical cavity for receiving distal end 30b of elongated shaft 30. As will be discussed in further detail below, first chamber 54 is configured such that distal end 30b of elongated shaft 30 is received pressed flush against insert 40. It is envisioned, however, that first chamber 54 may be configured such that distal end 30b of elongated shaft 30 is proximally spaced from insert 40. Intermediate chamber 56 defines a substantially cylindrical cavity configured to receive insert 40. Intermediate chamber 56 includes ribs or spacers 56a for maintaining insert 40 (shown in phantom in FIG. 7) centered within intermediate chamber 56. Insert 40 includes a solid, substantially cylindrical member positioned within intermediate chamber 56 to force the first and second precursors to flow around insert 40 in the space recreated by ribs 56a. It is envisioned that insert 40 may be sized to extend proximally from intermediate chamber 56 into first chamber 54 to ensure that insert 40 is received flush against distal end 30b of elongated shaft 30.

Figure 5:
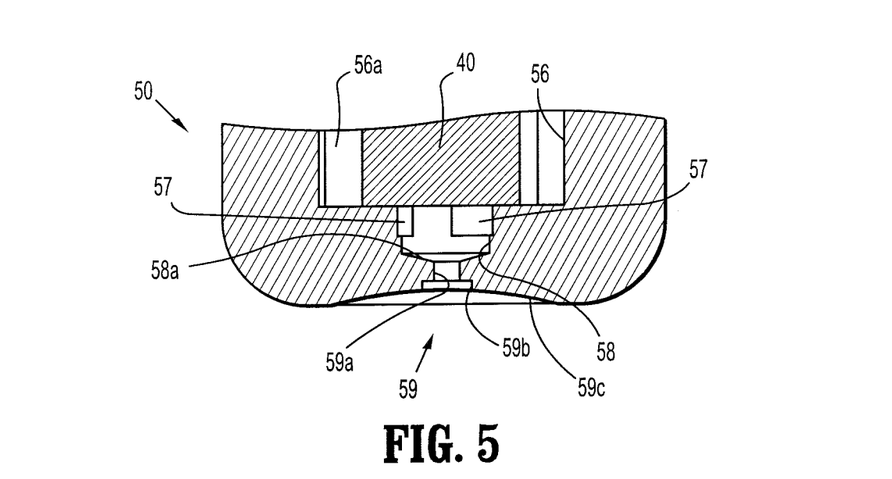
FIG. 5 is an enlarged cross-sectional view of the distal end of the spray tip assembly of FIG. 4.
Figure 6:
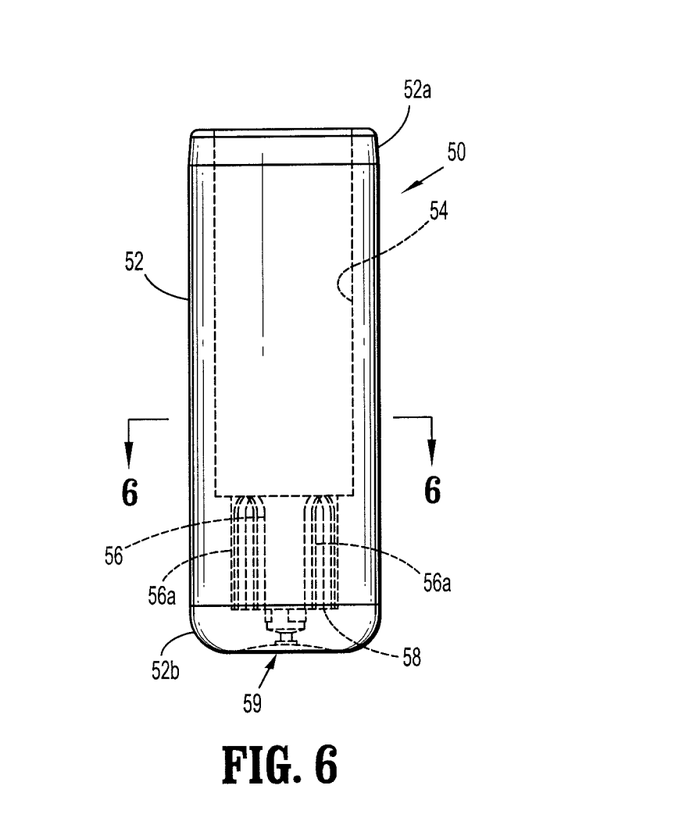
FIG. 6 is a side view of the spray tip assembly of FIGS. 4 and 5 with internal structure shown in phantom.
Figure 7:
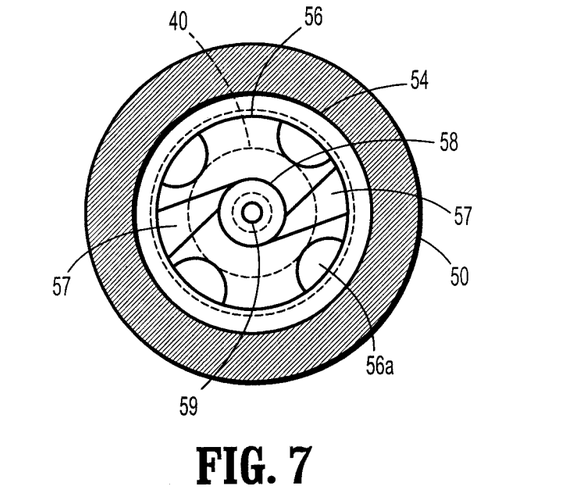
FIG. 7 is a cross-sectional view of the spray tip assembly of FIG. 6 taken along line 6-6.
Figure 7A:
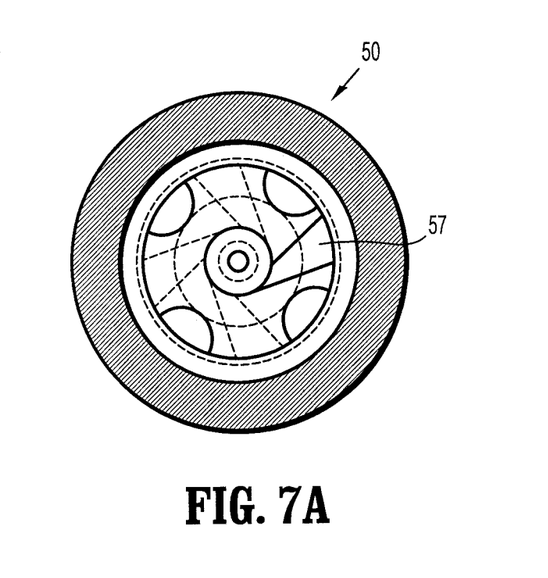
FIG. 7A is a cross-sectional view of an alternate embodiment of the spray tip of FIG. 7.

With reference still to FIGS. 4-7, final chamber 58 defines a substantially cylindrical cavity having a tapered distal portion 58a. Spray tip assembly 50 includes slots 57 formed therein fluidly communicating intermediate chamber 56 and final chamber 58. Slots 57 define opposed openings angling outwardly from final chamber 58 between a line tangent to final chamber 58 and about twenty degrees (20°) counterclockwise from the tangent line. Slots 57 direct the partially mixed first and second precursors from within intermediate chamber 56 into final chamber 58. Although shown as a pair of opposed openings, it is envisioned that spray tip assembly 50 may include only a single slot 57 (FIG. 7A), or may alternatively include three or more slots 57 (shown in phantom, FIG. 7A). Outlet 59 is configured to atomize the thoroughly mixed solution into a generally cone-shaped spray. As shown in FIG. 5, from proximal to distal, outlet 59 includes a first cylindrical portion 59a, a second cylindrical portion 59b, and a recessed portion 59c. It is envisioned, however, that outlet 59 may be formed without second cylindrical portion 59b.

Although shown with reference to spray tip assembly 50, any spray tip assembly configured for dispensing a material that gels may benefit from the aspects of the present disclosure. As discussed above, charged polymers assist in preventing premature gelling of various mixtures. In one embodiment, a charged polymer is integrally formed with spray tip assembly 50 to prevent premature gelling of the mixture passing therethrough. In an alternative embodiment, an inner surface of spray tip assembly 50 is coated with a charged polymer to assist in preventing premature gelling of the mixture passing therethrough. Insert 40 may also include a charged polymer either integrally formed therewith or as a coating thereon to further assist in preventing the premature gelling of the mixture passing through spray tip assembly 50. Means for applying such a coating are within the purview of those skilled in the art and include, but are not limited to, spraying, dipping, combinations thereof, and the like.

The operation of applicator assembly 10 will now be described as relates to the figures. Prior to use, insert 40 is received within intermediate chamber 56 of spray tip assembly 50. As discussed above, insert 40 is positioned such that fluid passing through intermediate chamber 56 is forced around insert 40 in the space created between ribs 56a. Spray tip assembly 50 is selectively received on distal end 30b of elongated shaft 30. As discussed above, manifold 20 may be integrally formed with elongated shaft 30, or instead it may be necessary to secure elongated shaft 30 to manifold 20 manually prior to use, making sure that first and second precursor channels 23, 25 are aligned with first and second precursor lumens 33, 35. First and second sources of precursor (not shown) are next connected to first and second proximal extensions 22, 24, respectively. Once secured to manifold 20, first and second sources of precursor may be activated, e.g., depression of syringe plungers, or other mechanical means including air and gas assisted sprayers, dynamic mixers, and the like (not shown), to initiate the flow of first and second precursors within first and second precursor channels 23, 25, respectively. The first and second precursors flow through first and second precursor channels 23, 25, through first and second precursor lumen 33, 35, respectively, and into spray tip assembly 50.

The first and second precursors flowing from first and second precursor lumens 33, 35 encounter insert 40 retained with intermediate chamber 56. First and second precursor lumens 33, 35 are spaced such that the first and second precursors may flow around insert 40 in the space created between ribs 56a and insert 40. The first and second precursors are then forced into slots 57 where they are directed radially inward toward final chamber 58. The flow of the mixture through slots 57 imparts a swirling motion to the mixture as the mixture enters final chamber 58. Thereafter, the thoroughly mixed solution is atomized as it is ejected through outlet 59 in a cone-shaped spray. As discussed above, spray tip assembly 50 and/or insert 40 includes, either formed integrally therewith or as a coating thereon, a charged polymer to prevent premature gelling of the mixture.

Figure 8:
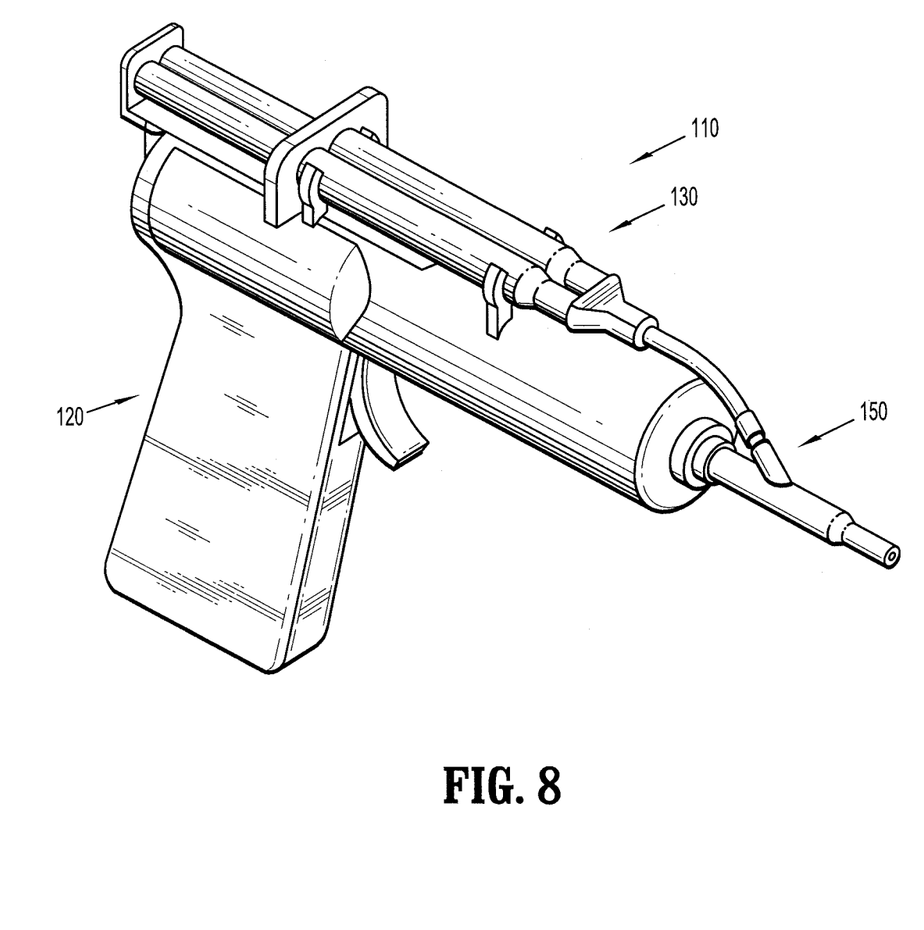
FIG. 8 is an alternate embodiment of an applicator assembly incorporating aspects of the present disclosure.
Figure 9:
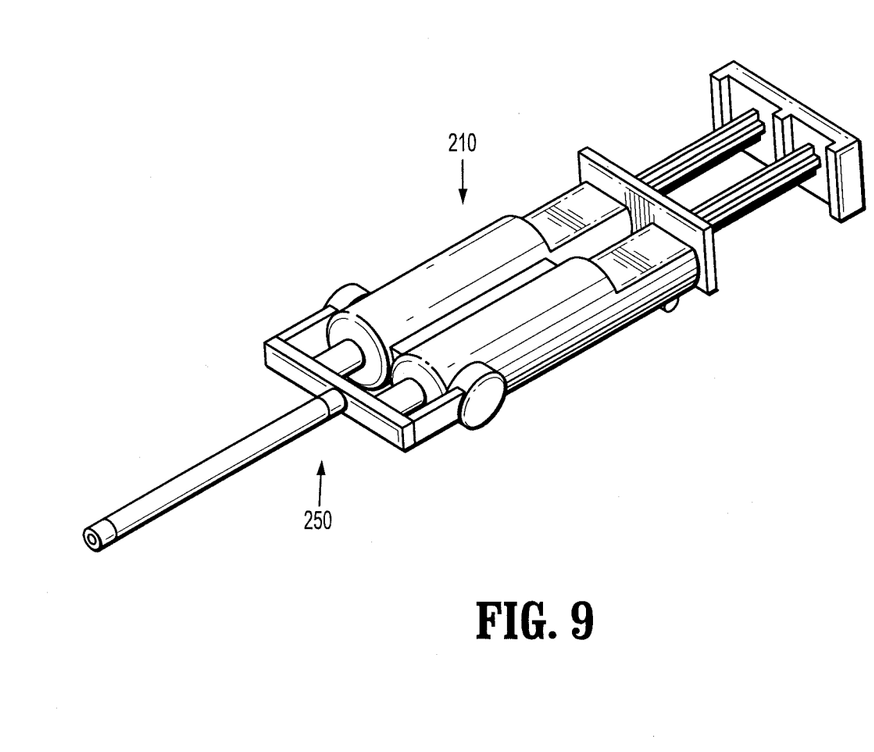
FIG. 9 is another embodiment of an applicator assembly incorporating aspects of the present disclosure.
Figure 10:
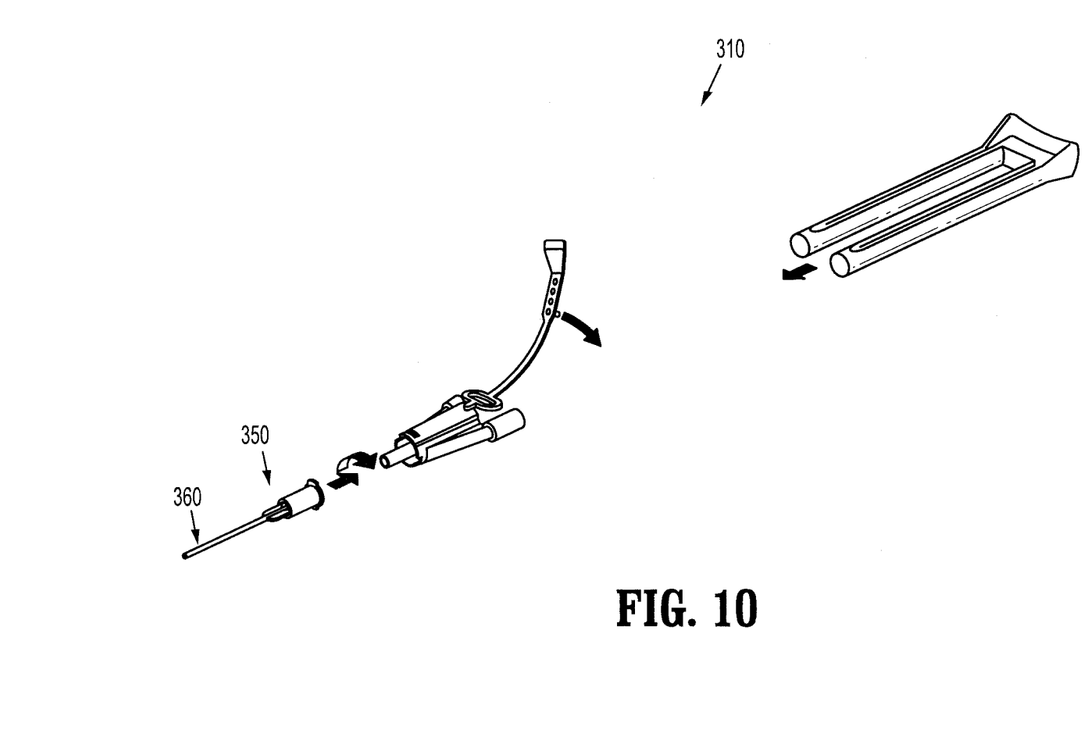
FIG. 10 is yet another embodiment of an applicator assembly incorporating aspects of the present disclosure.

With reference now to FIGS. 8-10, alternate embodiments of applicator assemblies benefiting from the aspects of the present disclosure are shown.

Referring initially to FIG. 8, applicator assembly 110 includes a housing 120 configured for pistol-grip engagement by a user, a fluid supply source 130 operably connected to housing 120 and a nozzle assembly 150 extending distally from housing 120. As with applicator assembly 10, described hereinabove, applicator assembly 110 is configured to mix and dispense a mixture composed of at least a first and a second component. Applicator assembly 110 is substantially similar in form and function to the applicator assembly described in commonly owned U.S. patent application Ser. No. 12/422,639, filed Apr. 13, 2009, the entire disclosure of which is incorporated by reference herein in its entirety.

Still referring to FIG. 8, to prevent premature gelling of the mixture being dispensed from applicator assembly 110, in one embodiment, a charged polymer is integrally formed with nozzle assembly 150 as well as the portions of fluid supply source 130 through which the mixture of first and second components flow. In an alternative embodiment, an inner surface of nozzle assembly 150 and portions of fluid supply source 130 through which the mixture of first and second components flow are coated with a charged polymer to prevent premature gelling of the mixture passing therethrough.

Turning to FIG. 9, an applicator assembly substantially similar to applicator assembly 10 described hereinabove is shown generally as applicator assembly 210. In one embodiment, a mixing and spraying assembly 250 of applicator assembly 210 is at least partially formed of a charged polymer such that a mixture passing therethrough is prevented from prematurely gelling. Alternatively, at least an inner surface of mixing and spraying assembly 250 are coated with a charged polymer to prevent premature gelling of the mixture passing therethrough.

With reference to FIG. 10, another applicator assembly for dispensing a mixture of a first and a second component is shown generally as applicator assembly 310. In one embodiment, a mixing and needle assembly 350 of applicator 310 may be at least partially formed of a charged polymer such that the mixture passing therethrough is prevented from prematurely gelling. Alternatively, at least an inner surface of mixing and needle assembly 350 is coated with a charged polymer to prevent premature gelling of the mixture passing therethrough.

In accordance with the present disclosure, a delivery device capable of preventing premature gelling of the precursor(s) of a pH dependent forming material may extend the time for application of the pH dependent forming material. This may permit introduction of the pH dependent forming material over a longer period of time, without having to worry about clogging/premature gelling if it becomes necessary to briefly stop during the introduction of the pH dependent forming material and then continue with its introduction.

The delivery device of the present disclosure may reduce or eliminate delays that may otherwise occur due to premature gel formation and/or clogging of the applicator, as well as undesirable properties of the resulting gel, such as the formation of two or more layers, gels with reduced strength or performance, uneven coatings, combinations thereof, and the like. In some cases, where an applicator includes multiple tips, the need to swap applicator tips during the introduction of a pH dependent forming material may be avoided. This will be a benefit to the health care provider introducing the pH dependent forming material, as it will provide for easier application of the pH dependent forming materials and improve both the consistency and outcome of surgical procedures utilizing the pH dependent forming materials.

While preferred illustrative embodiments of the disclosure are described above, it will be apparent to one skilled in the art that various changes and modifications may be made therein without departing from the disclosure and it is intended in the appended claims to cover all such changes and modifications which fall within the true spirit and scope of the disclosure. For example, any of the above disclosed applicator assemblies may be configured to utilize air as a means for assisting in the expulsion of mixture therefrom. Additionally, any tubing extending from the applicator assemblies for applying a mixture remotely may be formed of a material having a surface functionality capable of modulating the pH of the materials near the surface, as well as the pH of the microenvironment near the surface of the device.

What is claimed is:

1. A delivery device comprising:
    at least one lumen;
    a means for aiding in expelling pH dependent forming materials from the lumen; and
    an opening configured to expel the pH dependent forming materials from the delivery device in vivo,
    wherein at least a portion of a surface of the delivery device comprises a charged polymer for modulating pH of a microenvironment near the surface thereby minimizing premature gelling of the pH dependent forming materials in contact with the surface and minimizing clogging of the delivery device.

2. The delivery device of claim 1, wherein the charged polymer comprises a coating on at least a portion of the surface of the lumen in contact with the materials.

3. The delivery device of claim 1, wherein the charged polymer possesses a negative charge.

4. The delivery device of claim 1, wherein the charged polymer possesses a positive charge.

5. The delivery device of claim 1, wherein the charged polymer is selected from the group consisting of 2-hydroxyethyl methacrylate, 2-acrylamido-2-methylpropane sulfonic acid, 3-methacryloylaminopropyl-trimethyl ammonium chloride, and combinations thereof.

6. The delivery device of claim 1, wherein the charged polymer comprises a positively charged copolymer of 3-methacryloylaminopropyl-trimethyl ammonium chloride with 2-hydroxyethyl methacrylate.

7. The delivery device of claim 1, wherein the charged polymer comprises a negatively charged copolymer of 2-acrylamido-2-methylpropane sulfonic acid with 2-hydroxyethyl methacrylate.

8. The delivery device of claim 1, wherein the charged polymer is selected from the group consisting of hydroxypropyl methylcellulose, methacrylic acid copolymers, and combinations thereof, in combination with an acid.

9. The delivery device of claim 8, wherein the charged polymer comprises a copolymer of methacrylic acid with ethyl acrylate.

10. The delivery device of claim 8, wherein the acid is selected from the group consisting of citric acid, fumaric acid, succinic acid, malic acid, and combinations thereof, present in an amount from about 0.1 percent by weight to about 10 percent by weight of the copolymer.

11. The delivery device of claim 1, wherein the delivery device further comprises:
    a manifold configured for operable engagement with at least a first and a second source of precursor of the material, the manifold including at least a first and second precursor channel therethrough; and
    a tip assembly,
    wherein the tip assembly is configured to receive a mixture comprising the at least first and second precursors prior to the mixture being expelled from an opening defined in a distal end of the tip assembly.

12. The delivery device of claim 11, wherein the tip assembly comprises a charged polymer.

13. The delivery device of claim 12, wherein the charged polymer comprises a coating on the tip assembly.

14. The delivery device of claim 11, wherein the device further comprises an elongated shaft extending distally from the manifold, the elongated shaft including at least a first and a second precursor lumen extending the length thereof, the at least first and second precursor lumens in fluid communication with the at least first and second precursor channels.

15. The delivery device of claim 14, wherein the tip assembly defines a first chamber, an intermediate chamber and a final chamber, wherein the first chamber is configured to receive a distal end of the elongated shaft, the intermediate chamber is configured to receive an insert, and the final chamber is configured to receive the at least partially mixed at least first and second precursors prior to the mixture being ejected from the opening defined in the distal end of the tip assembly.

16. The delivery device of claim 15, wherein the insert comprises silicone.

17. The delivery device of claim 14, wherein the manifold and elongated shaft are integrally formed.

18. The delivery device of claim 14, wherein the elongated shaft is flexible.

19. The delivery device of claim 14, wherein the elongated shaft comprises silicone.

20. The delivery device of claim 11, wherein the opening is configured to eject the mixture from the tip assembly as a spray.

21. The delivery device of claim 11, wherein the tip assembly comprises silicone.

22. The delivery device of claim 11, wherein the tip assembly is configured to flex during operation.

* * * * *